(12) United States Patent
Luan et al.

(10) Patent No.: US 10,094,805 B2
(45) Date of Patent: Oct. 9, 2018

(54) INCREASING THE CAPTURE ZONE BY NANOSTRUCTURE PATTERNS

(71) Applicant: International Business Machines Corporation, Armonk, NY (US)

(72) Inventors: Binquan Luan, Chappaqua, NY (US); Gustavo A. Stolovitzky, Riverdale, NY (US); Chao Wang, Ossining, NY (US); Deqiang Wang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/583,501

(22) Filed: May 1, 2017

(65) Prior Publication Data

US 2017/0234833 A1    Aug. 17, 2017

Related U.S. Application Data

(62) Division of application No. 14/271,926, filed on May 7, 2014, now Pat. No. 9,658,184.

(51) Int. Cl.
| | |
|---|---|
| *G01N 1/10* | (2006.01) |
| *G01N 27/447* | (2006.01) |
| *G01N 33/487* | (2006.01) |
| *C12Q 1/6869* | (2018.01) |

(52) U.S. Cl.
CPC ..... *G01N 27/44791* (2013.01); *C12Q 1/6869* (2013.01); *G01N 33/48721* (2013.01)

(58) Field of Classification Search
None
See application file for complete search history.

(56) References Cited

U.S. PATENT DOCUMENTS

| | | |
|---|---|---|
| 6,368,871 B1 | 4/2002 | Christel et al. |
| 7,217,562 B2 | 5/2007 | Cao et al. |
| 7,777,505 B2 | 8/2010 | White et al. |
| 8,003,319 B2 | 8/2011 | Polonsky et al. |
| 8,070,928 B2 | 12/2011 | Sundberg et al. |

OTHER PUBLICATIONS

J. Han et al., "Entropic trapping and escape of long DNA molecules at submicron size constriction," Physical Review Letters, vol. 83, No. 8, pp. 1688-1691, Aug. 1999.

(Continued)

*Primary Examiner* — Xiaoyun R Xu
(74) *Attorney, Agent, or Firm* — Vazken Alexanian; Michael J. Chang, LLC

(57) ABSTRACT

Techniques for increasing the capture zone in nano and microchannel-based polymer testing structures using concentric arrangements of nanostructures, such as nanopillars are provided. In one aspect, a testing structure for testing polymers is provided that includes a first fluid reservoir and a second fluid reservoir formed in an electrically insulating substrate; at least one channel formed in the insulating substrate that interconnects the first fluid reservoir and the second fluid reservoir; and an arrangement of nanostructures within either the first fluid reservoir or the second fluid reservoir wherein the nanostructures are arranged so as to form multiple concentric circles inside either the first fluid reservoir or the second fluid reservoir with each of the concentric circles being centered at an entry point of the channel. A method of analyzing a polymer using the testing structure is also provided.

16 Claims, 7 Drawing Sheets

(56) References Cited

OTHER PUBLICATIONS

M. Wanunu et al., "Electrostatic focusing of unlabelled DNA into nanoscale pores using a salt gradient," Nature Nanotechnology, vol. 5, No. 2, pp. 160-165, Dec. 2009 (6 total pages).

W. Reisner et al., "DNA confinement in nanochannels: physics and biological applications," Reports on Progress in Physics, vol. 75, No. 10, 106601, Sep. 2012 (34 total pages).

N.C. Cady et al., "Nucleic acid purification using microfabricated silicon structures," Biosensors and Bioelectronics, vol. 19, No. 1, pp. 59-66, Oct. 2003.

M. Tsutsui et al., "Transverse electric field dragging of DNA in a nanochannel," Scientific Reports, vol. 2, No. 394, 7 pages, May 2012.

G.C. Randall et al., "DNA deformation in electric fields: DNA driven past a cylindrical obstruction," Macromolecules, vol. 38, No. 6, pp. 2410-2418, Feb. 2005.

S.W.P. Turner et al., "Confinement-Induced Entropic Recoil of Single DNA Molecules in a Nanofluidic Structure," Physical Review Letters, vol. 88, No. 8, 128103, Mar. 2002 (4 total pages).

Uba, F.I. et al., "Nanogap Electrical Detection of Single Molecules Translocating Through a Nanochannel With Transverse Nanoelectrodes and Funnels Populated With an Array of Nanopillars," 15th International Conference on Miniaturized Systems for Chemistry and Life Sciences Oct. 2-6, 2011, Seattle, Washington, USA, pp. 401-403.

Menard, L.D. et al., A Device for Performing Lateral Conductance Measurements on Individual Double-Stranded DNA Molecules, 2012, ACS Nano, vol. 6(10), pp. 9087-9094.

List of IBM Patents or Applications Treated as Related (2 pages).

round nanochannel resulting from selective removal of the nanowire from the filler material longest diagonal of rectangular channel can be used as $r_0$ for calculations diagonal of square nanopillar can be used as D for calculations longest edge of triangular nanopillar can be used as D for calculations

INCREASING THE CAPTURE ZONE BY NANOSTRUCTURE PATTERNS

CROSS-REFERENCE TO RELATED APPLICATION(S)

This application is a divisional of U.S. application Ser. No. 14/271,926 filed on May 7, 2014, the disclosure of which is incorporated by reference herein.

FIELD OF THE INVENTION

The present invention relates to nano and microchannel-based polymer testing structures, and more particularly, to techniques for increasing the capture zone in nano and microchannel-based polymer testing structures using concentric arrangements of nanostructures, such as nanopillars.

BACKGROUND OF THE INVENTION

A nanochannel typically has a round or square cross-section with a width, side, etc. of about 50 nanometers (nm) to about 100 nm, and a length of from about 1 micrometer (μm) to about 5 μm. See, for example, W. Reisner et al., "DNA confinement in nanochannels: physics and biological applications," *Reports on Progress in Physics* 75, 106601 (September 2012) (hereinafter "Reisner").

A nanochannel can provide a platform to study molecular behaviors at the single molecule scale. Namely, the nanochannel can sort, manipulate, and detect the DNA samples. See, for example, Reisner and J. Han et al., "Entropic Trapping and Escape of Long DNA Molecules at Submicron Size Constriction," *Physical Review Letters* 83, 1688-1691 (August 1999) (hereinafter "Han"). As described in Han, an electric field is used to drive passage of DNA molecules through a microfabricated channel. With the process described in Han, however, the electric field will decay a distance 1/r away from the entry of the channel (wherein r is the radius of cross-section of channel) thereby limiting its utility.

Previously, different methods have been proposed to enhance the translocations of DNA for nanofluidic systems, such as a salt gradient and high voltages. See, for example, M. Wanunu et al., "Electrostatic focusing of unlabelled DNA into nanoscale pores using a salt gradient," *Nature Nanotechnology* 5, 160-165 (2010) (published December 2009). These methods however only change the electric field distribution close to the nanoscale pore entry.

Thus, techniques which expand the electric field of entry into a nanochannel and thereby increase the capture zone and capture rate of the nanochannel for processes such as DNA sequencing would be desirable.

SUMMARY OF THE INVENTION

Techniques for increasing the capture zone in nano and microchannel-based polymer testing structures using concentric arrangements of nanostructures, such as nanopillars are provided. In one aspect of the invention, a testing structure for testing polymers is provided. The testing structure includes a first fluid reservoir and a second fluid reservoir formed in an electrically insulating substrate; at least one channel formed in the insulating substrate that interconnects the first fluid reservoir and the second fluid reservoir; and an arrangement of nanostructures within either the first fluid reservoir or the second fluid reservoir wherein the nanostructures are arranged so as to form multiple concentric circles inside either the first fluid reservoir or the second fluid reservoir with each of the concentric circles being centered at an entry point of the channel.

In another aspect of the invention, a method of analyzing a polymer is provided. The method includes the steps of: providing a testing structure having a first fluid reservoir and a second fluid reservoir interconnected by at least one nanochannel, an electrolyte solution within the first fluid reservoir, the second fluid reservoir and the nanochannel, and an arrangement of nanostructures within the first fluid reservoir, wherein the nanostructures are arranged so as to form multiple concentric circles inside the first fluid reservoir with each of the concentric circles being centered at an entry point of the nanochannel; placing the polymer within the first fluid reservoir; applying a voltage to the first fluid reservoir and the second fluid reservoir to create an electrical force to move the polymer through the arrangement of nanostructures and into the nanochannel; and monitoring ionic current changes in the electrolyte solution as the polymer passes through the nanochannel to obtain ionic current data for one or more constituent components of the polymer.

A more complete understanding of the present invention, as well as further features and advantages of the present invention, will be obtained by reference to the following detailed description and drawings.

DETAILED DESCRIPTION OF PREFERRED EMBODIMENTS

Techniques are provided herein which integrate nanostructures and nanochannels together where the nanostructures increase the capture zone of the nanochannels and enhance the capture rate for the nanochannel. The present techniques will pave the way for sequencing DNA with nanopore and nanochannel technologies. While the description below mentions the capture of deoxyribonucleic acid (DNA) molecules for sequencing, the present techniques may be applied, in the same manner described, to any polymer for which capture in a nanochannel is desired. By way of example only, polymers such as single-stranded DNA or RNA, double-stranded DNA or RNA, peptides or other linear polymers may be analyzed using the present techniques.

Figure 1:
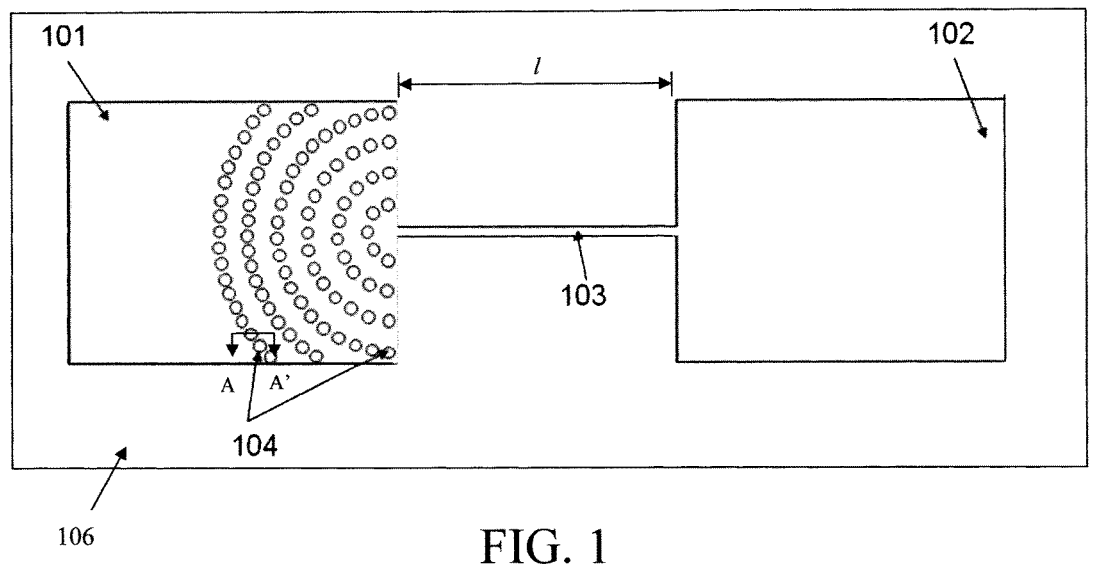
FIG. 1 is a top-down diagram illustrating an exemplary nanochannel-based testing structure that may be used for DNA sequencing according to an embodiment of the present invention.

An overview of the present techniques will now be provided by way of reference to FIGS. 1-6. FIG. 1 is a diagram illustrating a nanochannel-based testing structure 100 formed in an (electrically) insulating substrate 106 having a first fluid reservoir 101 connected to a second fluid reservoir 102 by at least one nanochannel 103. Namely, a fluid can pass between the reservoirs 101, 102 via the nanochannel 103.

Suitable electrically insulating materials for forming substrate 106 include, but are not limited to, silicon oxide or silicon nitride. By way of example only, the testing structure 100 can be fabricated (as described in detail below) starting with a bulk semiconductor wafer (such as a bulk silicon wafer) having an insulator layer thereon which can serve as the insulating substrate 106. A variety of different configurations that will yield an insulating substrate upon which the testing device 100 can be constructed would be within the capabilities of one skilled in the art.

By way of example only, the term "nanochannel" as used herein can refer to a channel having a rectangular (e.g., square) or round cross-section with at least one dimension when viewed in cross-section (such as a diameter for round channels or a diagonal for rectangular and square channels) that is from about 1 nanometer (nm) to about 100 nm and ranges therebetween, and a length l of from about 100 nm to about 5 micrometer (μm) and ranges therebetween. This is, however, only an example. The present techniques can be implemented to increase the capture zone and capture rate of any size channel. For instance, rather than a nanochannel 103, the channel connecting the reservoirs 101 and 102 might be a microchannel with a rectangular (e.g., square) or round cross-section with at least one dimension when viewed in cross-section (such as a diameter for round channels or a diagonal for rectangular and square channels) that is from about 1 μm to about 100 μm and ranges therebetween, and a length l of from about 1 μm to about 50 μm and ranges therebetween.

The reservoirs 101, 102 and the nanochannel 103 are filled with an electrolyte solution. Suitable electrolyte solutions include, but are not limited to, potassium chloride (KCl) or sodium chloride (NaCl) solutions.

Figures 2, 3, 4:
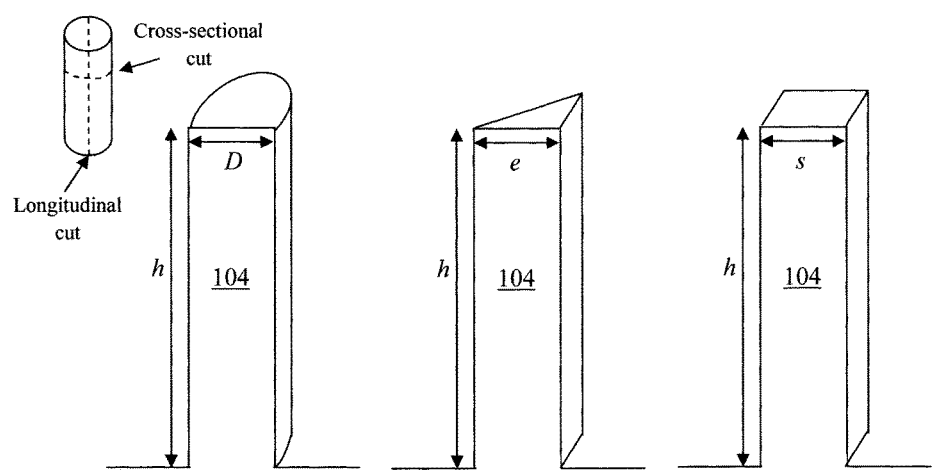
FIG. 2 is a diagram of longitudinal cut through a nanopillar (having a round cross-section when viewed from the top down) according to an embodiment of the present invention.
FIG. 3 is a diagram of longitudinal cut through a nanopillar having a triangular cross-section when viewed from the top down according to an embodiment of the present invention.
FIG. 4 is a diagram of a longitudinal cut through a nanopillar having a rectangular (e.g., square) cross-section when viewed from the top down according to an embodiment of the present invention.
Figure 5:
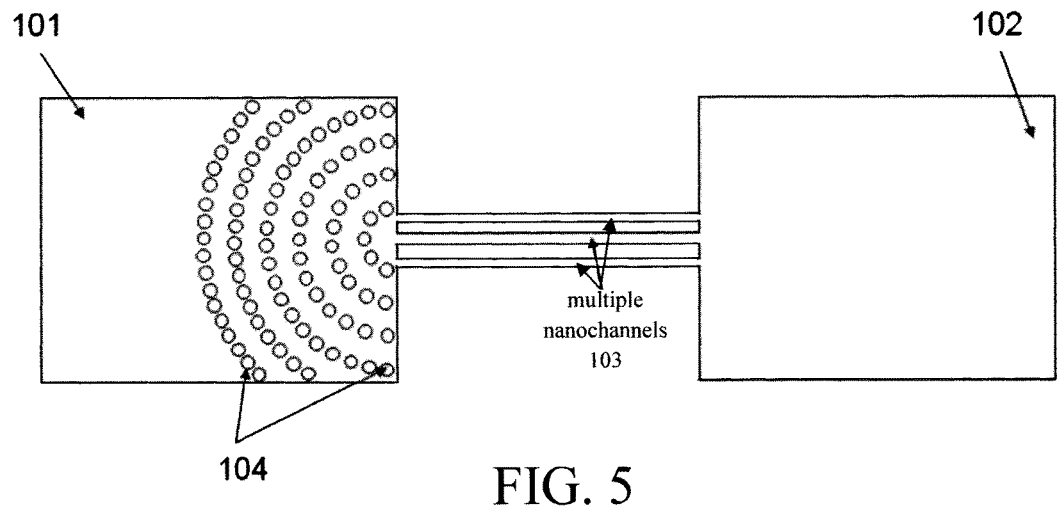
FIG. 5 is a top-down diagram illustrating an exemplary configuration of the present testing structure having multiple nanochannels according to an embodiment of the present invention.
Figure 6:
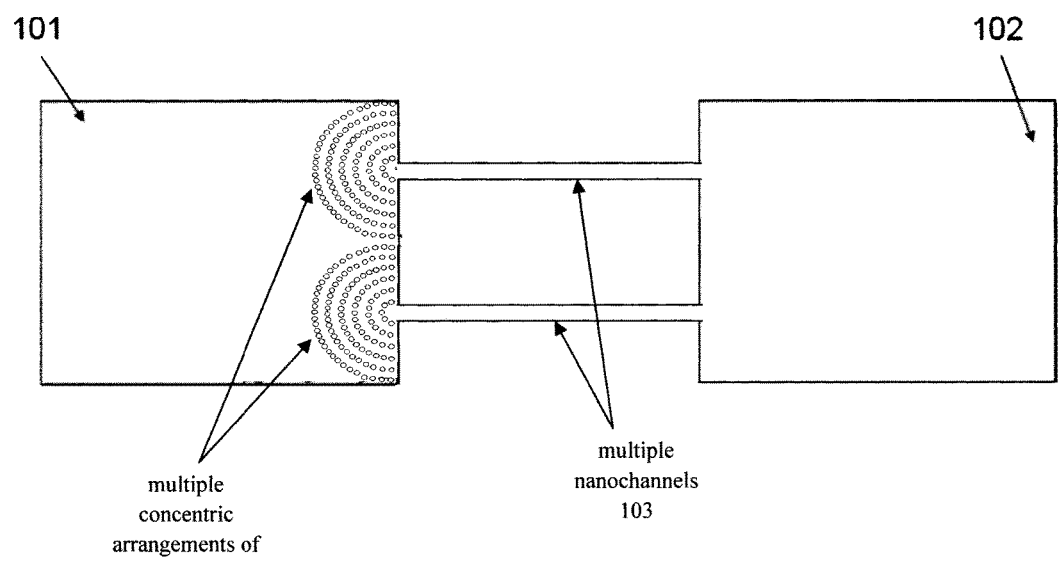
FIG. 6 is a top-down diagram illustrating an exemplary configuration of the present testing structure having multiple concentric arrangements of nanostructures and multiple nanochannels according to an embodiment of the present invention.

A concentric arrangement of nanostructures (also referred to herein as a nanostructure region) is present at the entrance to the nanochannel 103 in one of the reservoirs (e.g., reservoir 101 in the example depicted in FIG. 1). In the example shown in FIG. 1, the nanostructures are nanopillars (having a round, triangular, rectangular (e.g., square), etc. cross-sectional shape—see FIGS. 2-4, respectively). The term "nanopillar" as used herein generally refers to a high-aspect-ratio pillar-shaped structure having, for example, a diameter D of from about 10 nanometers (nm) to about 100 nm and ranges therebetween, and a height h of from about 20 nm to about 5 micrometers (μm) and ranges therebetween. See, for example FIG. 2. FIG. 2 depicts a longitudinal cut (i.e., along a line A-A' see FIG. 1) through one of the nanopillar nanostructures 104. As will be described in detail below, the nanostructures may be patterned from the insulating substrate 106 in the corresponding reservoir. Thus, in that case, the nanostructures are formed from the same insulating material (e.g., silicon oxide or nitride) as the substrate. While the nanopillars shown in FIG. 1 have a round cross-sectional shape when viewed from the top down, this is merely one example. Nanopillars having different shapes (e.g., a triangular, square, etc. cross-section when viewed from the top down) may be formed and used in the same manner as described herein. For completeness, a nanopillar nanostructure 104 having a triangular cross-section (with height h of, e.g., of from about 20 nm to about 5 μm and ranges therebetween, and edge e of, e.g., from about 10 nm to about 100 nm and ranges therebetween) is shown in FIG. 3, and a nanopillar nanostructure 104 having a rectangular (i.e., square) cross-section (with height h of, e.g., of from about 20 nm to about 5 µm and ranges therebetween, and side s of, e.g., from about 10 nm to about 100 nm and ranges therebetween) is shown in FIG. 4.

During operation of the testing structure 100, a polymer (such as deoxyribonucleic acid (DNA)) is introduced into the reservoir having the concentric arrangement of nanopillars and an electrical force is used to pull the polymer into the nanochannel 103. The nanopillars aid in capturing the polymer, and by way of their concentric arrangement, serve to direct the polymer toward an entrance to the nanochannel 103. Thus, the nanopillar arrangement effectively increases the capture zone in the reservoir. Further, interaction of DNA molecules with the nanopillars 104 prior to entering the nanochannel 103 helps to uncoil (i.e., linearized) the molecule. The uncoiled molecule may then be fed through the channel and analyzed.

It is notable that while FIG. 1 illustrates use of a device having a single nanochannel, this is merely one possible configuration. For instance, the present techniques may be applied to multi-channel configurations, such as those shown illustrated in FIG. 5 and FIG. 6. In the example shown in FIG. 5, a single concentric arrangement of the nanostructures 104 is used to direct a polymer into one of multiple adjacent nanochannels 103. In the example shown in FIG. 6, multiple concentric arrangements of nanopillars are used to direct a polymer into one of multiple adjacent nanochannels 103 (e.g., wherein a first concentric arrangement of nanostructures 104 serves to direct a polymer into a first nanochannel, a second concentric arrangement of nanostructures 104 serves to direct a polymer into a second nanochannel, etc.). For ease and clarity of description, the embodiment consisting of a single nanochannel and a single concentric arrangement of nanostructures is used in the description that follows. However, these multi-channel nanostructure embodiments may be produced and used, and thus function in the same manner as described.

Figure 7:
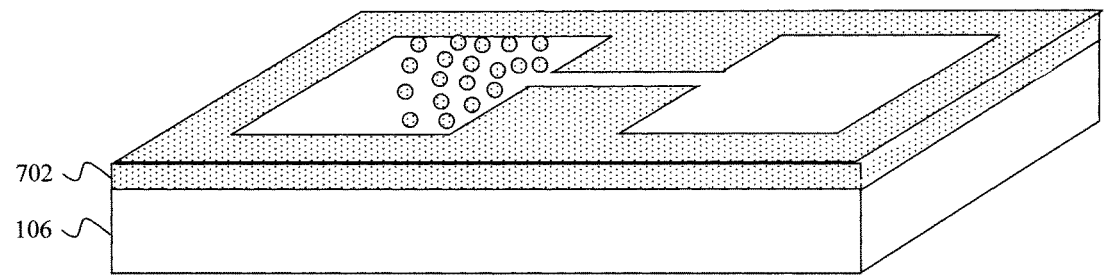
FIG. 7 is a three-dimensional diagram illustrating a starting structure for fabricating the present testing structure having an insulating substrate and a resist on the substrate patterned with the footprint and location of the reservoirs, the nanochannel, and the concentric arrangement of nanostructures according to an embodiment of the present invention.
Figure 8:
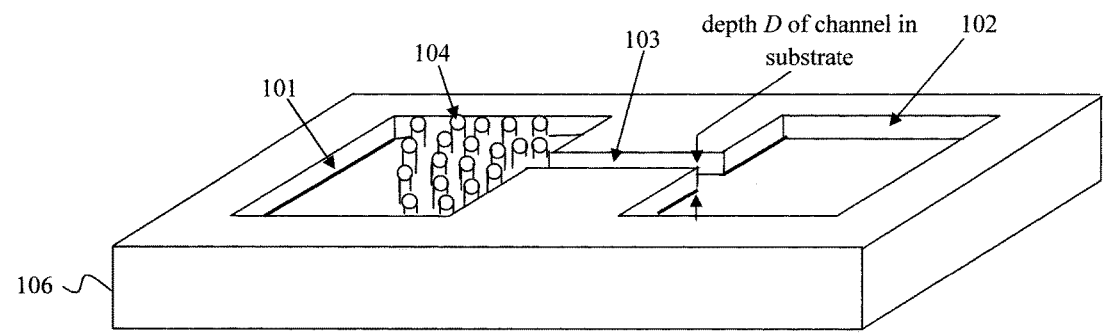
FIG. 8 is a three-dimensional diagram illustrating the resist having been used to pattern the reservoirs, the nanochannel, and the concentric arrangement of nanostructures in the insulating substrate, and the resist having been removed according to an embodiment of the present invention.
Figure 9:
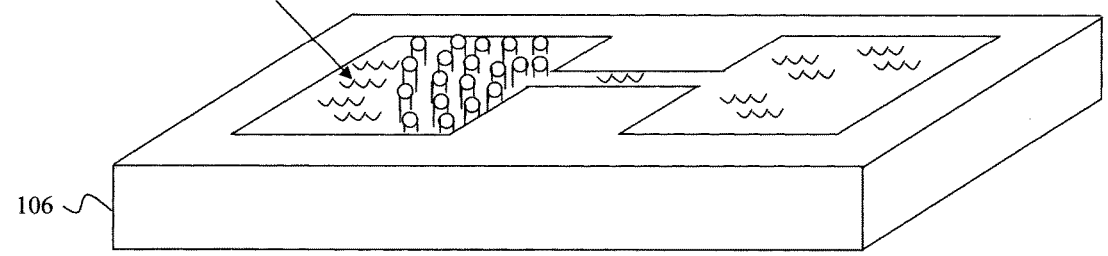
FIG. 9 is a three-dimensional diagram illustrating an electrolyte having been added to the reservoirs and the nanochannel according to an embodiment of the present invention.

An exemplary methodology for fabricating the present testing structure is now described by way of reference to FIGS. 7-9. As highlighted above, the fabrication process begins with an insulating (e.g., silicon oxide, silicon nitride, etc.) substrate 106. See FIG. 7. The insulating substrate 106 may be part of a larger wafer structure which would be apparent to one skilled in the art and thus not shown in the present figures.

Lithography and etching processes are then used to pattern the reservoirs 101, 102, the nanochannel(s) 103 and the nanostructures 104 in the insulating substrate 106. According to an exemplary embodiment, the reservoirs 101, 102, the nanochannel(s) 103 and the nanostructures 104 are all patterned at the same time using an e-beam lithography process. E-beam lithography involves patterning a resist 702 on the insulating substrate 106 with the footprint and location of the reservoirs 101, 102, the nanochannel(s) 103 and the nanostructures 104. See FIG. 7. The patterned resist is then used to pattern the insulating substrate 106. Following patterning of the insulating substrate 106, the resist can be stripped. See FIG. 8.

Suitable e-beam resist materials include, but are not limited to, poly methyl methacrylate (PMMA). By comparison with optical lithography, e-beam lithography is well suited for forming complex patterns, such as nanostructures and nanochannels. Rather than patterning the resist using a mask (as with optical lithography), e-beam lithography (a maskless process) involves emitting a beam of electrons in a patterned fashion to pattern the resist. By way of example only, direct write e-beam systems employ an e-beam spot that is moved with respect to the substrate being patterned to expose the substrate one pixel at a time. Accordingly, very complex and intricate patterns can be created using e-beam lithography. Optical lithography may also be adapted and employed to create the present testing structure, if so desired, but does require an extra masking step.

Figure 15:
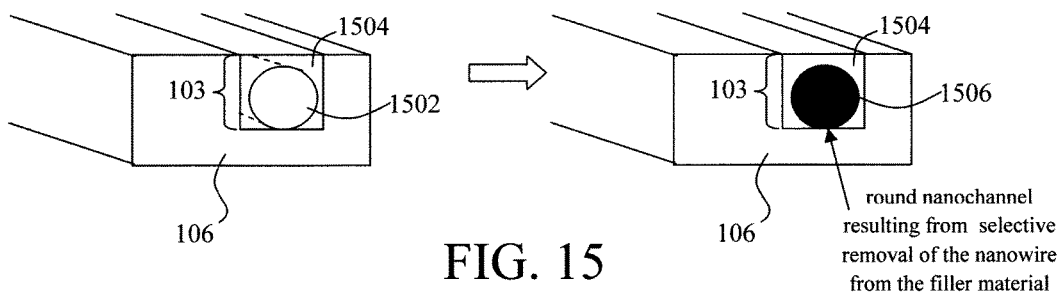
FIG. 15 is a three-dimensional diagram illustrating the formation of a round nanochannel according to an embodiment of the present invention.
Figure 16A:
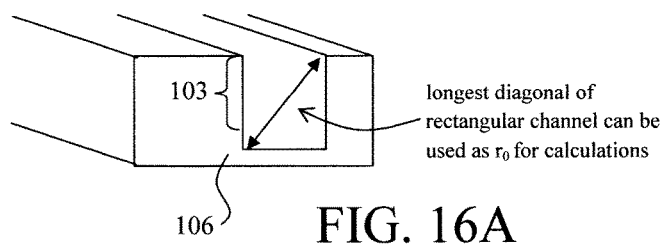
FIG. 16A is a three-dimensional diagram illustrating use of a longest length diagonal to represent $r_0$ of a rectangular nanochannel according to an embodiment of the present invention.

Patterning the nanochannel(s) (and reservoirs, nanostructures, etc.) in the manner described above will result in the nanochannel(s) each having approximately a rectangular (e.g., square) cross-sectional shape. See, for example, FIG. 16A—described below. While a rectangular or square cross-sectional shaped nanochannel is suitable according to the present techniques, it is possible to create different shaped nanochannels (e.g., round nanochannels) in the device, if so desired (see FIG. 15). By way of example only, beginning with the device structure shown in FIG. 8 (resulting from the above-described process), as shown in FIG. 15 a round nanochannel can be created by depositing a nanowire 1502 on the insulating substrate 106 within, and along the length of, the nanochannel 103. In order to form a round nanochannel, the nanowire 1502 should have a round (cross-sectional) shape. Preferably, the nanowire 1502 is made of a material that can be etched selective to an insulator, such as a silicon nanowire. The nanowire 1502 in the nanochannel 103 is then buried in an insulating filler material 1504, such as silicon dioxide. According to an exemplary embodiment, the insulating filler material 1504 used is the same (insulator) material as insulating substrate 106. A selective etch, e.g., xenon difluoride ($XeF_2$), is then used to remove the (e.g., silicon) nanowire 1502 selective to the insulator (i.e., the insulating filler material 1504 and the insulating substrate 106), resulting in a round nanochannel 1506 having been formed in the filler material 1504.

Referring back to FIG. 8, according to an exemplary embodiment, the nanostructures patterned (in the above-described manner) all have the same size and shape as one another, and thus have the same dimensions (e.g., same height, diameter, edge, width, etc.) as one another. Further, according to an exemplary embodiment, a depth D of the (rectangular) nanochannel(s) 103 patterned in the insulating substrate 106 (see FIG. 8) is the same as the height h (see FIGS. 2-4) of the nanostructures 104 (i.e., D=h). Patterning these nanostructures 104 to the same depth within the insulating substrate 106 advantageously enables the use of a single etching process to create the device (as well as insures a seamless transition of testing molecules from the reservoir into the channel—see below).

FIG. 9 is a three-dimensional diagram illustrating an electrolyte solution having been added to the reservoirs which are interconnected by the nanochannel(s). As provided above, suitable electrolyte solutions include, but are not limited to, (e.g., aqueous) KCl or NaCl solutions. According to an exemplary embodiment, the electrolyte solution is added in an amount sufficient to completely fill the reservoirs and the nanochannel(s).

Figure 10:
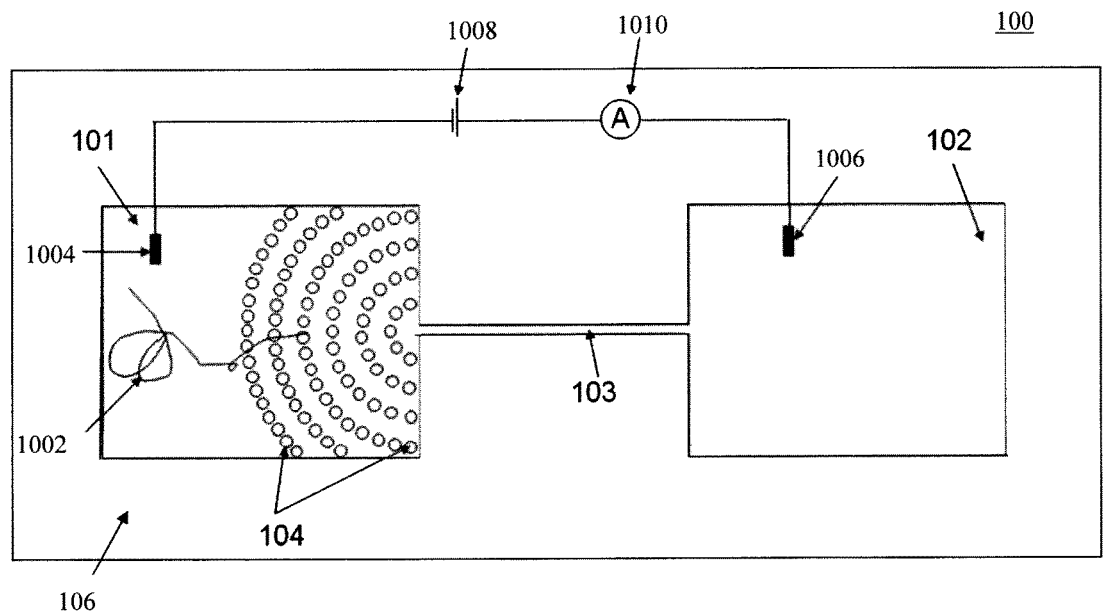
FIG. 10 is a top-down diagram illustrating use of the present testing structure for analyzing a linear polymer, wherein the polymer is injected into one of the reservoirs and the nanostructures in the reservoir aid in capturing and linearizing the polymer according to an embodiment of the present invention.
Figure 11:
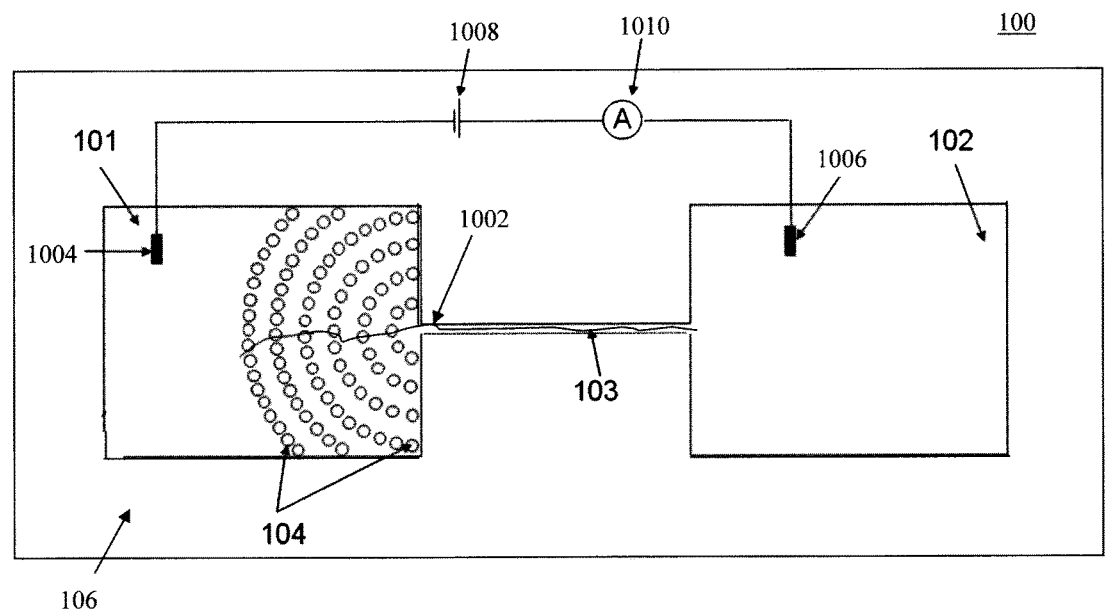
FIG. 11 is a top-down diagram which, following from FIG. 10, illustrates an electrical force between electrodes in the reservoirs drawing the (linearized) polymer through the nanochannel where changes in ionic current can be monitored according to an embodiment of the present invention.

An exemplary method for using the present testing structure/device to analyze a linear polymer is now described by way of reference to FIGS. 10 and 11. For ease and clarity of depiction, the perspective shown in the figures now reverts back to a top-down view of the device 100. As shown in FIG. 10, a linear polymer 1002, such as single or double stranded DNA or RNA, peptides, etc., is first placed (e.g., injected) into reservoir 101. As provided above, the interconnected reservoirs 101, 102 and nanochannel(s) 103 are filled with an electrolyte (e.g., KCl or NaCl) solution.

Electrodes 1004 and 1006 are present in reservoirs 101 and 102, respectively. By way of example only, the electrodes 1004 and 1006 can be silver/silver chloride (Ag/AgCl) reference electrodes, platinum electrodes, etc. The electrodes 1004 and 1006 are connected to a voltage source 1008. The concept being employed here is that a charged molecule such as DNA, RNA, etc. will change the ionic current through the nanochannel as the molecule passes through the channel. Thus, an ammeter 1010 is preferably located in circuit with the electrodes 1004 and 1006 as shown in FIG. 10.

The electrical force between the electrodes 1004 and 1006 will pull the polymer 1002 through the array of nanostructures 104. As shown in FIG. 11, the polymer 1002 will be captured and linearized when it moves into the region of the nanostructures 104. As shown in FIG. 11, due to the shape of the nanochannel 103, the polymer 1002 will keep its linearized status when it passes through the nanochannel 103.

Figure 12:
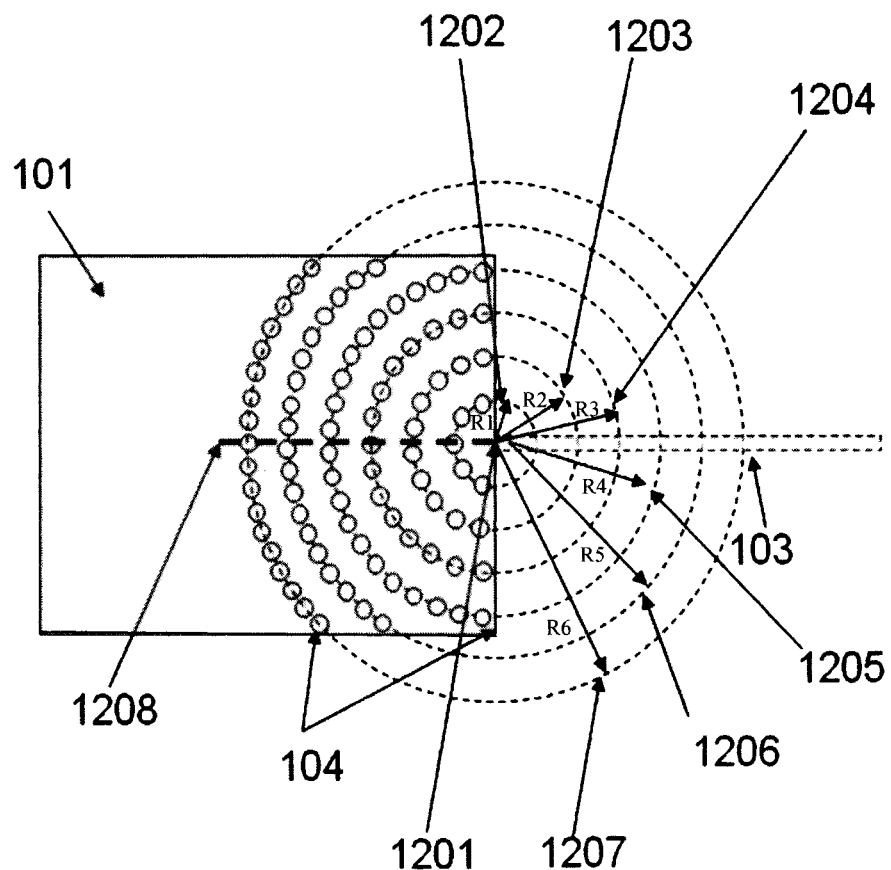
FIG. 12 is a top-down diagram illustrating an exemplary arrangement of the array of nanostructures forming multiple concentric circles inside the reservoir with each of the concentric circles being centered at an entry point of the nanochannel according to an embodiment of the present invention.
Figure 13:
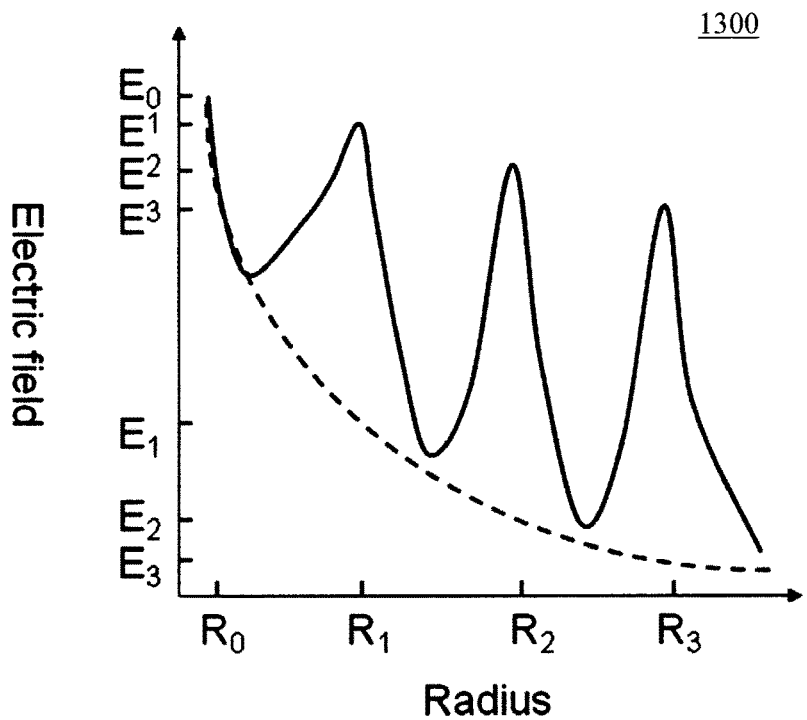
FIG. 13 is a chart illustrating the destitutions of electric field with and without a concentric arrangement of nanopillars according to an embodiment of the present invention.

The principle of increasing the capture zone in the testing structure with the array of nanostructures 104 is now described by way of reference to FIGS. 12 and 13. With regard to FIG. 12, the reservoir (in this case reservoir 101) having the nanostructures 104 and the nanochannel 103 are shown. As highlighted above, a concentric arrangement of the nanostructures 104 is present in one of the reservoirs at the entrance to the nanochannel 103.

According to an exemplary embodiment, the nanostructures 104 are arranged so as to form multiple concentric circles 1202, 1203, ..., 1207, etc. inside the reservoir 101 with each of the concentric circles being centered at an entry point 1201 of the nanochannel 103. See FIG. 12.

Figure 12A:
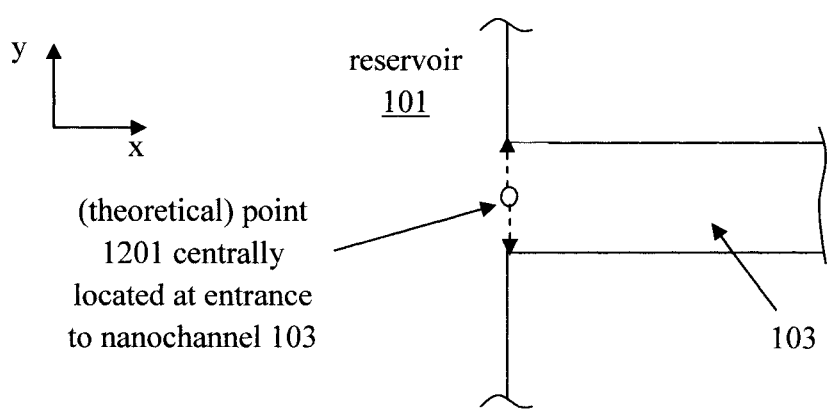
FIG. 12A is a schematic diagram showing an enlarged view of the nanochannel and reservoir which illustrates how the concentric circles may be centered at a (theoretical) point centrally located at the entrance to the nanochannel according to an embodiment of the present invention.

According to an exemplary embodiment, the entry point 1201 is centrally located at the entrance of the nanochannel 103 (see FIG. 12A which provides a magnified view of the entrance to the nanochannel 103). As shown in FIG. 12, the concentric circles 1202, 1203, ..., 1207, etc. of nanostructures 104 are each centered at entry point 1201 of the nanochannel 103 and have different radii from R1 to R2, R3, R4, R5, R6, etc. Of course the number of nanostructures and/or the number of rings of concentric circles can vary depending on the size of the reservoir, and multiple regions of concentrically arranged nanopillars may be formed when, for instance, multiple nanochannels are present (see, for example, FIG. 6—described above) with each concentric arrangement being centered at the entry point to one of the nanochannels.

Figure 16B:
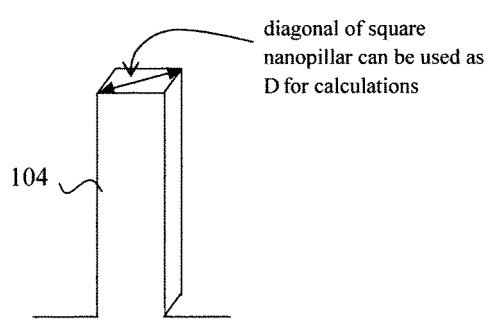
FIG. 16B is a three-dimensional diagram illustrating use of a diagonal length to represent D of a square nanopillar according to an embodiment of the present invention.
Figure 16C:
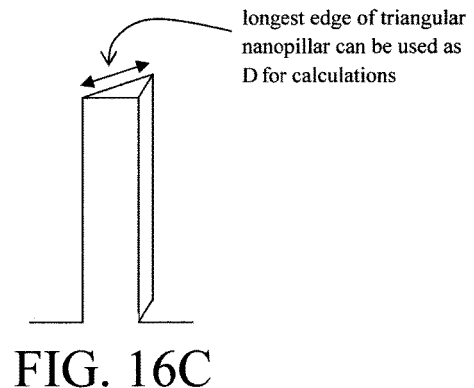
FIG. 16C is a three-dimensional diagram illustrating use of a longest length edge to represent D of a triangular nanopillar according to an embodiment of the present invention.

While including a greater number of concentric rings of the nanostructures in the respective reservoir (potentially even filling one of the reservoirs with (concentrically arranged) nanopillars) will increase the capture zone in the reservoir, as illustrated in the figures it is not necessary to completely fill the reservoir with nanostructures to receive the benefits of the present techniques. A formula is provided below for calculating the electric field (in the device) based on the dimensions of the nanostructures and the nanochannel. By way of example only, if the radius of the nanochannel is 100 nm and the diameter of each of the nanopillars is 150 nm, then having from 3 to 5 rings of nanostructures in the reservoir will provide a capture zone at a micrometer scale. It is notable that while this computation is based on the radius of a (round) nanochannel and the diameter of (round) nanostructures, as highlighted above, the nanochannel and/or the nanostructures can have non-round shapes. Notwithstanding, the calculations can be applied in the same manner to these other (non-round) nanochannel and nanostructure configurations. See, FIGS. 16A-C, below.

FIG. 13 is a chart 1300 illustrating the distribution of electric field with and without nanopillars 104 along the dashed line 1208 (see FIG. 12). In chart 1300, the electric field $E^1$, $E^2$, and $E^3$ are the electric field inside reservoir 101 with radius at $R_1$, $R_2$, and $R_3$ of the present centrically arranged nanopillars (see FIG. 12), respectively. By comparison, $E_1$, $E_2$, and $E_3$ are the electric field inside reservoir 101 at the same radii $R_1$, $R_2$, and $R_3$ from the entry point 1201 to the nanochannel 103 but when no nanostructures are present in the reservoir 101. As is clear from chart 1300, the electric field in the reservoir 101 at $R_1$, $R_2$, and $R_3$ is significantly greater when the present concentrically arranged nanopillars are employed as described herein.

It is assumed in this example that the nanostructures each have the same shape and dimensions (e.g., same height h, same length diameter d, edge e, or width w—see FIGS. 2-4) and that the depth of the nanochannel 103 (see, for example, FIG. 8) is the same as the height h of the nanostructures (to insure a seamless passage of the polymer through the array of nanostructures and into the channel). According to an exemplary embodiment, if the radius of the nanochannel 103 is $r_0$, then the number of nanostructures 104 at the distance r from the entrance point of the nanochannel 103 is $r/r_0$. Thus using a simple (non-limiting) example, if the radius of the nanochannel 103 is 1 nanometer (nm), and distance R1 is 5 nm, then 5 (i.e., 5/1) nanostructures 104 would be located a distance R1 from the entrance to the nanochannel. If the distance R2 from the entrance to the nanochannel 103 is 10 nm, then 10 (i.e., 10/1) nanostructures 104 would be located a distance R2 from the entrance to the nanochannel, and so on. This exemplary configuration is illustrated in FIG. 12. Again, it is acknowledged that these computations are based on the radius of a (round) nanochannel and the diameter of (round) nanostructures. However, as highlighted above, the nanochannel and/or the nanostructures can have non-round shapes. Notwithstanding, these calculations can be applied in the same manner to these other (non-round) nanochannel and nanostructure configurations. See, FIGS. 16A-C, below.

Because the electric field strength E is inversely proportional to the cross-sectional area of the nanochannel available for ionic current, then $E \sim 1/(1-D/\pi r_0)*1/r$, wherein D is nanopillar diameter. Thus, using this formula, if D (nanopillar diameter) is $0.9*\pi r_0$, the electric field is enhanced by 10 times because of the presence of pillars. Again, it is noted that these computations are based on the radius of a (round) nanochannel and the diameter of (round) nanostructures. However, as highlighted above, the nanochannel and/or the nanostructures can have non-round shapes. Notwithstanding, these calculations can be applied in the same manner to these other (non-round) nanochannel and nanostructure configurations. See, FIGS. 16A-C, below. For example, in the case where a non-round channel or pillar shape is employed, the variables such as $r_0$ and D can be calculated based on the actual dimensions of the structures. According to an exemplary embodiment, the greatest/longest dimension of the structure when viewed in cross-section (i.e., the diameter D for round nanopillars (see FIG. 2) and/or round nanochannels, the longest edge e for triangle-shaped nanopillars (see FIG. 3), or the longest length diagonal for square or rectangular-shaped nanopillars (see FIG. 4) and/or square or rectangular nanochannels) is used in the calculations. This concept is further illustrated by way of reference to FIGS. 16 A-C, described below.

Figure 14:
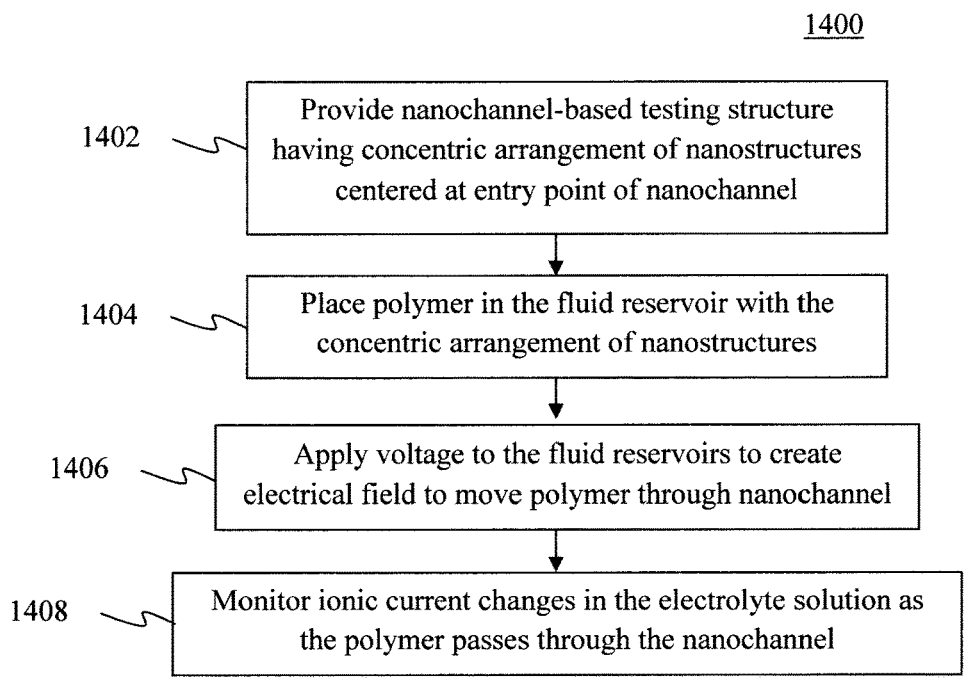
FIG. 14 is a diagram illustrating an exemplary methodology for use of the present testing structure to analyze a polymer according to an embodiment of the present invention.

FIG. 14 is a diagram illustrating an exemplary methodology 1400 for use of the present testing structure to analyze a polymer (e.g., single or double stranded DNA/RNA, peptide, etc.). In step 1402, one of the present testing structures is provided. The details of the nanostructures, channel(s), electrolyte solution, etc. and other configurations of the present testing structures were provided above. Further, use of the present nanochannel-based testing structure was depicted in FIGS. 10 and 11 (described above).

Any of the present testing structure configurations described above may be employed. For instance, the testing structure may include a first fluid reservoir and a second fluid reservoir interconnected by at least one nanochannel, an electrolyte solution within the first fluid reservoir, the second fluid reservoir and the nanochannel, and an arrangement of nanostructures within the first fluid reservoir. The nanostructures are arranged so as to form multiple concentric circles inside the first fluid reservoir with each of the concentric circles being centered at an entry point of the nanochannel.

In step 1404, the polymer (e.g., single or double stranded DNA/RNA, peptide, etc.) is placed within (e.g., injected into) the first fluid reservoir. In step 1406, a voltage is applied to the first fluid reservoir and the second fluid reservoir by way of a pair of first/second electrodes (e.g., electrodes 1004/1006) placed in the first/second fluid reservoirs, respectively. As provided above, the applied voltage will create an electrical force between the electrodes to move the polymer through the arrangement of nanostructures and into the nanochannel. The present concentric arrangement of nanostructures, as provided above, aids in increasing the capture zone, and serves to uncoil the polymer sample. In step 1408, ionic current changes in the electrolyte solution are monitored as the polymer passes through the nanochannel.

This process can be used to analyze the properties of the polymer. By way of example, only, the polymer can be long chain DNA, RNA, or a protein. In that case, the present techniques can be used to detect or sequence constituent components (e.g., nucleotides or amino acids) in the polymer based on the ionic current changes when they (i.e., the particular nucleotides or amino acids in the polymer) pass through the nanochannel. Namely, due to the differences in size and conformation of a single nucleotide and amino acid, individual components (e.g., nucleotide or amino acid) of the polymer (e.g., DNA, RNA, or protein) can be discerned based on the ionic current detected when the particular component passes through the channel. Thus, as the polymer passes through the channel, a change in the ionic current indicates a change in the particular component of the polymer currently passing through the channel. This ionic current data obtained for the constituent components of the polymer can be used for a variety of different analyses, such as identifying the constituent components of the polymer— i.e., so as to be able to sequence the polymer, or more broadly to distinguish one constituent component from another—e.g., determine the number of different components in a given polymer.

Some of the above-described calculations, such as those for determining electric field in the presence of the nanopillars include variables such as channel radius $r_0$ and nanopillars diameter D. These are straightforward measurements for round channels and nanopillars. However, as provided above, the channel(s) and/or the nanopillars might have a different (non-round) shape. For instance, as provided above, the nanochannel(s) might instead have a rectangular (e.g., square) (cross-sectional) shape and/or the nanopillars might instead have a triangular or square (cross-sectional) shape. Nonetheless, the same calculations still apply. In the case of non-round nanochannels and/or nanopillars, in one exemplary embodiment, one simply uses the greatest (i.e., longest) cross-sectional dimension of the structure in the calculations. Take for instance the exemplary nanochannel shown in FIG. 16A which has a rectangular shape when viewed in cross-section and the exemplary nanopillar shown in FIG. 16B which has a square shape when viewed in cross-section. The longest dimension, i.e., the longest diagonal of the (rectangular channel, square nanopillar, etc.) can be used as the values for channel radius $r_0$ and nanopillar diameter D, respectively. The same principles can be applied for square nanochannels and rectangular nanopillars. Similarly, with the exemplary nanopillar shown in FIG. 6C, which has a triangular shape when viewed in cross-section, the longest dimension, i.e., the longest edge of the triangular nanopillar can be used as the value for nanopillar diameter D.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A testing structure for testing polymers, comprising:
a first fluid reservoir and a second fluid reservoir formed in an electrically insulating substrate, wherein the first fluid reservoir has a square shape with four sides;
at least one channel formed in the insulating substrate that interconnects the first fluid reservoir and the second fluid reservoir, wherein the channel connects with the first fluid reservoir along one of the sides; and
an arrangement of nanostructures within the first fluid reservoir wherein the nanostructures are arranged so as to form multiple concentric circles inside the first fluid reservoir with each of the concentric circles being centered at an entry point of the channel.

2. The testing structure of claim 1, further comprising:
an electrolyte solution within the first fluid reservoir, the second fluid reservoir and the channel.

3. The testing structure of claim 2, wherein the electrolyte solution is selected from the group consisting of: a potassium chloride solution and a sodium chloride solution.

4. The testing structure of claim 1, wherein the channel comprises a nanochannel having a round or square cross-sectional shape having at least one cross-sectional dimension that is from about 1 nm to about 100 nm and ranges therebetween, and a length of from about 100 nm to about 5 µm and ranges therebetween.

5. The testing structure of claim 1, wherein the channel comprises a microchannel having a round or square cross-sectional shape having at least one cross-sectional dimension that is from about 1 µm to about 100 µm and ranges therebetween, and a length of from about 1 µm to about 50 µm and ranges therebetween.

6. The testing structure of claim 1, wherein the nanostructures comprise nanopillars each having a height of from about 20 nanometers to about 5 micrometers and ranges therebetween.

7. The testing structure of claim 1, wherein the nanostructures are formed from a same material as the electrically insulating substrate.

8. The testing structure of claim 6, wherein each of the nanopillars has a round cross-sectional shape with a diameter D of from about 10 nanometers to about 100 nanometers and ranges therebetween.

9. The testing structure of claim 6, wherein each of the nanopillars has a triangular cross-sectional shape with an edge e of from about 10 nanometers to about 100 nanometers and ranges therebetween.

10. The testing structure of claim 6, wherein each of the nanopillars has a square cross-sectional shape with an width w of from about 10 nanometers to about 100 nanometers and ranges therebetween.

11. The testing structure of claim 1, wherein all of the nanostructures in the testing structure have a same shape and same dimensions as one another.

12. The testing structure of claim 1, wherein the channel has a depth D and each of the nanostructures has a same height h, and wherein D=h.

13. The testing structure of claim 1, wherein the channel has a round cross-sectional shape with a radius $r_0$ and wherein a number of the nanostructures at a distance r from the entry point of the channel is $r/r_0$.

14. The testing structure of claim 1, further comprising:
a first electrode present in the first fluid reservoir and a second electrode present in the second fluid reservoir; and
a voltage source connected to both the first electrode and the second electrode.

15. The testing structure of claim 14, further comprising:
an ammeter, wherein the voltage source is connected in circuit with the first electrode, the second electrode, and the ammeter.

16. The testing structure of claim 1, comprising multiple channels formed in the insulating substrate that interconnect the first fluid reservoir and the second fluid reservoir.

\* \* \* \* \*